US008618050B2

(12) United States Patent
Shulman et al.

(10) Patent No.: US 8,618,050 B2
(45) Date of Patent: Dec. 31, 2013

(54) LIPID PREPARATION FOR ENHANCING MINERAL ABSORPTION

(75) Inventors: Avidor Shulman, Kiryat Tivon (IL); Gai Ben Dror, Moshav Ofer (IL); Dori Pelled, Hod HaSharon (IL)

(73) Assignee: Enzymotec Ltd., Migdal Haemeq (IL)

(*) Notice: Subject to any disclaimer, the term of this patent is extended or adjusted under 35 U.S.C. 154(b) by 698 days.

(21) Appl. No.: 10/576,239

(22) PCT Filed: Oct. 21, 2004

(86) PCT No.: PCT/IL2004/000961
§ 371 (c)(1), (2), (4) Date: Feb. 5, 2007

(87) PCT Pub. No.: WO2005/037373
PCT Pub. Date: Apr. 28, 2005

(65) Prior Publication Data
US 2008/0058415 A1   Mar. 6, 2008

(30) Foreign Application Priority Data

Oct. 22, 2003 (IL) .......................................... 158555

(51) Int. Cl.
*A61K 38/00* (2006.01)
(52) U.S. Cl.
USPC .......................................................... 514/7.4
(58) Field of Classification Search
None
See application file for complete search history.

(56) References Cited

U.S. PATENT DOCUMENTS

| | | | |
|---|---|---|---|
| 3,542,560 A | 11/1970 | Tomarelli et al. | |
| 4,876,107 A | 10/1989 | King et al. | |
| 5,000,975 A | 3/1991 | Tomarelli | |
| 5,371,253 A | 12/1994 | Cooper | |
| 5,601,860 A | 2/1997 | Lien et al. | |
| 5,658,768 A | 8/1997 | Quinlan | |
| 5,709,888 A | 1/1998 | Gil et al. | |
| 6,248,909 B1 | 6/2001 | Akimoto et al. | |
| 6,292,792 B1 | 9/2001 | Baffes et al. | |
| 6,863,918 B2 | 3/2005 | Bindels et al. | |
| 2003/0072865 A1 | 4/2003 | Bindels et al. | |
| 2004/0137072 A1 | 7/2004 | Cockrum | |
| 2007/0218169 A1 | 9/2007 | Meiri-Bendek | |
| 2008/0058415 A1 | 3/2008 | Shulman | |

FOREIGN PATENT DOCUMENTS

| | | |
|---|---|---|
| CA | 2357459 A1 | 10/2002 |
| CN | 1152856 A | 6/1997 |
| EP | 0209327 | 1/1987 |
| EP | 0209327 A2 | 1/1987 |
| EP | 0376628 | 7/1990 |
| EP | 0 495 456 | 7/1992 |
| EP | 0495456 | 7/1992 |
| EP | 0496456 A1 | 7/1992 |
| EP | 0 882 797 | 12/1998 |
| EP | 0 965 578 | 12/1999 |
| EP | 1 062 873 | 12/2000 |
| EP | 1 252 824 | 10/2002 |
| WO | 9426854 | 11/1994 |
| WO | 9531110 A1 | 11/1995 |
| WO | WO 95/31110 | 11/1995 |
| WO | WO-00/56869 | 9/2000 |
| WO | 00/58869 | 10/2000 |

OTHER PUBLICATIONS

Kennedy, Kathy, et al., Double blind, randomized trial of a synthetic triacylglycerol in formula fed term infants: effects on stool biochemistry, stool characteristics, and bone mineralization, Am Journal of Clinical Nutrition 1999, 70:920-7.*
Kennedy et al. Double blind, randomized trial of a synthetic triacylglycerol in formula fed term infant: effect on stool biochemistry, stool characteristics, and bone mineralization.*
FoodIngredientFirst, Enzymotec launches InFat perfect fat for infant formula, available online Apr. 7, 2003.*
Spurgeon et al. An Investigation of the general, reproductive and postnatal developmental toxicity of Betapol, a human milk fat equivalent, available online Aug. 2, 2003.*
Zampelas et al. The effect of triacylglycerol fatty acid positional distribution on postprandial plasma metabolite and hormone responses in normal adult men, Sep. 14, 1992. British Journal of Nutrition (1994), 71, 401-410.*
Zock et al., Partial conservation of the sn-2 position of dietary triglyercides in fasting plasma lipids in humans, European Journal of Clinical Investigation (1996), 26, p. 141-150.*
International Search Report published on Apr. 28, 2005 for PCT/IL04/00961 (to which this application claims priority).
Written Opinion published on Apr. 22, 2006 for PCT/IL04/00961(to which this application claims priority).
International Prelim. Report on on Patentability published on Apr. 22, 2006 for PCT/IL04/00961(to which this application claims priority).
International Search Report published on Apr. 28, 2005 for PCT/IL04/00960 (both PCT/IL04/00961 and PCT/IL04/00960 claim priority to IL 158555).
Lucas A., Arch. Dis. Child., 1997, pp. F178-F184, vol. 77.
Susan E. Carlson, Phd, et. al., Docosahexaenoic acid status of preterm infants at birth and following feeding with human milk or formula, Am. J. Clin. Nutri., 1986, pp. 798-804, v.44, American Society for Clinical Nutrition.

(Continued)

*Primary Examiner* — Anand Desai
*Assistant Examiner* — Melissa Mercier
(74) *Attorney, Agent, or Firm* — Martin Fleit; Paul D. Bianco; Fleit Gibbons Gutman Bongini & Bianco PL

(57) ABSTRACT

Disclosed is a dietary ingredient comprising at least one edible lipid which does not inhibit mineral absorption, enhances mineral absorption and intake, particularly a chemically or enzymatically synthesized synthetic oil, particularly glyceride-based lipid with high levels of mono- or polyunsaturated fatty acids at positions sn-1 and sn-3 of the glycerol backbone, vegetable- and plant-derived oil, such as flax and canola oils, short and medium chains lipid, preferably MCT and an oil mimicking the triglyceride composition of human mother's milk fat and its various uses.
The dietary ingredient is particularly intended for use in enhancing calcium absorption and in the prevention and/or treatment of disorders associated with depletion of bone calcium and bone density, prevention and treatment of osteoporosis, for the enhancement of bone formation and bone mass maximization and for the enhancement of bone formation in infants and young children.

9 Claims, No Drawings

(56) References Cited

OTHER PUBLICATIONS

Virgilio P. Carnielli, et. al., Feeding premature newborn infants palmitic acid in amounts and stereoisomeric position similar to that of human milk: effect on fat and mineral balance, Am. J. Clin. Nutr., 1995, pp. 1037-1042, v. 61, American Society for Clinical Nutrition.
Virgilio P. Carnielli, et. al., Structural Position and Amount of Palmitic Acid in Infant Formulas: Effects on Fat, Fatty Acid, and Mineral Balance, Journal of Pediatric Gastroenterology and Nutrition, Dec. 1996, pp. 553-560, v. 23, n. 5.
L. J. Filer, Jr. et. al., Triglyceride Configuration and Fat Absorption by the Human Infant, J. Nutrition, 1969, pp. 293-298, v. 99.
Olle Hernell, et. al., Digestion and Absorption of Human Milk Lipids, Perinatal Nutrition, 1988, pp. 259-272.
Sheila M. Innis, et. al., Plasma and red blood cell fatty acids of low-birth-weight infants fed their mother's expressed breast milk or preterm-infant formula, Am. J. Clin. Nutr., 1990, pp. 994-1000, v. 51, American Society for Clinical Nutrition.
Sheila M. Innis, et. al., Saturated fatty acid chain length and positional distribution in infant formula: effects on growth and plasma lipids and ketones in piglets, Am. J. Clin. Nutr., 1993, pp. 382-390, v. 57, American Society for Clinical Nutrition.
Sheila M. Innis, Phd et. al., Effects of Developmental Changes and Early Nutrition on Cholesterol Metabolism in Infancy: A Review, Journal of the American College of Nutrition, 1992, pp. 63S-68S, v. 11, n. 2.
B. Koletzko, et. al., Effects of dietary long-chain polyunsaturated fatty acids on the essential fatty acid status of premature infants, European Journal of Pediatrics, 1989, pp. 669-675, v. 148.
Eric L. Lien, et. al., The Effect of Triglyceride Positional Distribution on Fatty Acid Absorption in Rats, Journal of Pediatric Gastroenterology and Nutrition, Aug. 1997, pp. 167-174, v. 25, n. 2.
A. Lopez-Lopez, et. al., The influence of dietary palmitic acid triacylglyceride position on the fatty acid, calcium and magnesium contents of at term newborn faeces, Early Human Development, 2001, pp. S83-S94, v. 65 suppl.
A. Lucas, et. al., Randomised controlled trial of a synthetic triglyceride milk formula for preterm infants, Archives of Disease in Childhood, 1997, pp. F178-F184, v. 77.
Steven E. Nelson, et. al., Absorption of Fat and Calcium by Infants Fed a Milk-Based Formula Containing Palm Olein, Journal of the American College of Nutrition, 1998, pp. 327-332, v. 17, n. 4.
Steven E. Nelson, et. al., Palm olein in infant formula: absorption of fat and minerals by normal infants, American Journal Clinical Nutrition, 1996, pp. 291-296, v. 64.
Karin M. Ostrom, et. al., Lower Calcium Absorption in Infants fed Casein Hydrolysate- and Soy Protein-Based Infant Formulas Containing Palm Olein Versus Formulas without Palm Olein, Journal of the American College of Nutrition, 2002, pp. 564-569, v.21, n. 6.
Jane C. Putnam, et. al., The effect of variations in dietary fatty acid on the fatty acid composition of erythrocyte phosphatidylcholine and phosphatidylethanolamine in human infants, The American Journal of Clinical Nutrition, Jul. 1982, pp. 106-114, v. 36.
P. T. Quinlan, et. al., The Relationship between Stool Hardness and Stool Composition in Breast- and Formula-fed Infants, Journal of Pediatric Gastroenterology and Nutrition, 1995, pp. 81-90, v. 20.
Donald M. Small, The Effects of Glyceride Structure on Absorption and Metabolism, Annual Review Nutrition, 1991, pp. 413-434, v. 11.
J. P. Van Biervliet, et. al., Plasma apoprotein and lipd patterns in newborns: Influence of Nutritional factors, Acta. Paediatr. Scand., 1981, pp. 851-856, v.70.
Chi-Sun Wang, et. al., Studies on the Substrate Specificity of Purified Human Milk Bile Salt-activated Lipase, J. of Biological Chemistry, Aug. 10, 1983, pp. 9197-9202, v. 258, n. 15.
Elsie M. Widdowson, et. al., Body Gat of British and Dutch Infants, British Medical Journal, Mar. 22, 1975, pp. 653-655, v. 1.
Database Medline Online, USNLM, Nov. 15, 1997, Cadogan J. et. al.L "Milk intake and bone mineral acquisition in adolescent girls: randomised, controlled intervention trial.", XP002315046, database access No. NLM9390050.
Database Medline Online, USNLM, Oct. 2003, Volek Jeff S. et. al.: "Increasing fluid milk favorable affects bone mineral density responses to resistance training in adolescent boys.", XP002315047, database access No. NLM14520257.
Database Embase Online, Elsevier Science Pub., 2000, Gueguen L: "Calcium balance: Requirements, intake and bioavailability", XP002315048, database access No. EMB-2000369954.
Database Embase Online, Elsevier Science Pub., Sep. 1, 2003, Scholz-Ahrens K.E.: "Nutrients of milk and their relevance for health", XP002315049, Database access No. EMB-2003380690.
Database FSTA Online, IFIS, 1996, Anonymous: "Betapol, a breakthrough in infant formula fats." XP002315600, Database access No. 96-1-08-N0030.
Enzymotec launches InFat—perfect fat for infant formulas, Online, Jul. 4, 2003, XP002315599, Retrieved from Internet URL: www.foodingredientsfirst.com/newsmaker.
Database Biosis Online, Biosciences Info. Service, 1996, Carnielli Virgilio P., et. al.: "Structural position and amount of palmitic acid in infant formulas: Effects on fat, fatty acid, and mineral balance", XP002315050, Database access No. PREV199799383168.
Database FSTA Online, IFIS, 1999, Kennedy K. et. al: "Double-blind, randomized trial of a synthetic triacylglycerol in formula-fed term infants: effects on stool biochemistry, stool characteristics, and bone minealization.", XP002315051, Database access No. 2000-00-g0249.
Database Embase Online, Elsevier Science Pub., 1979, Jenness R: "The composition of Human Milk", XP002315052, Database access No. EMB-1979225226.
Database Medline Online, USNLM, Nov. 1997, Lucas A. et. al.: "Randomised controlled trial of a synthetic triglyceride milk formula for preterm infants.", XP002315783, access No. NLM9462186 & Archives of Disease in Childhood, Nov. 1997, vol. 77, No. 3, pp. F178-F184.
R. Jacobson, et. al., Effect of short-term high dietary calcium intake on 24-h energy expenditure, fat oxidation, and fecal fat excretion, International Journal of Obesity. 2005, pp. 292-301, v. 29.
Robert G. Jensen, The composition of Bovine Milk Lipids: Jan. 1995 to Dec. 2000, J. Dairy Sci., American Dairy Science Association, 2002, pp. 295-350, v. 85.
University of Maryland Med. Ctr. Web Site: http://www.umm.edu/home>medicalreference>alternative/complementarymedicine>tableofcontents>depletions>AntacidsAluminumCalciumand MagnesiumContainingPreparationscl.htm.
"Betapol" World of Ingredients, 1996, pp. 41-42, XP009043320.
Chappell J.E. et al., J. of Ped.,1986, pp. 439-447, vol. 108(3).
Hamosh M., Nutrition, 1990, pp. 421-428, vol. 6(6).
Hanna F.M. et al., Pediatrics, 1970, pp. 216-224, vol. 45(2).
Innis S.M. et al., Lipids, 1994, pp. 541-545, vol. 29(8).
Innis S.M. et al., J. Nutr., 1995, pp. 73-81, vol. 125.
Jensen C. et al., Am. J. Clin. Nutr., 1986, pp. 745-751, vol. 43.
Mattson F.H. et al., J. Biol. Chem., 1956, pp. 735-740, 219.
Tomarelli R.M. et al., J. Nutr., 1968, pp. 583-590, vol. 95.
Kennedy K. et al., Am. J. Clin. Nutr., 1999, pp. 920-927, vol. 70.
InFat TM 3070 Certificates of Analysis, Manufactured 2006-2008.
Carroll, Kenneth, K., "Upper Limits of Nutrients in Infant Formulas: Polyunsaturated Fatty Acids and Trans Fatty Acids," 1989, Journal of Nutrition, 119: 1810:1813.
Response to Office Action filed Jan. 27, 2011 for U.S. Appl. No. 10/576,240.
Response to Office Action filed Jul. 20, 2010 for U.S. Appl. No. 10/576,240.
Response to Office Action filed Oct. 19, 2009 for U.S. Appl. No. 10/576,240.
Response to Office Action filed Oct. 11, 2011 for U.S. Appl. No. 11/576,240.
Office Action dated Apr. 11, 2011 for U.S. Appl. No. 11/576,240.
Examiners Summary dated Apr. 5, 2011 for U.S. Appl. No. 11/576,240.
Copending U.S. Appl. No. 10/576,240, Office Action Sep. 27, 2010.
Copending U.S. Appl. No. 10/576,240, Office Action Feb. 22, 2010.
Copending U.S. Appl. No. 10/576,240, Non-Final Rejection Jun. 18, 2009.

(56) References Cited

OTHER PUBLICATIONS

Zock, P.L. et al, Partial conservation of the sn-2 position of dietary triglycerides in fasting plasma lipids in humans, European Journal of Clinical Investigation (1996) 26, 141-150.
Haumann, Barbara Fitch, Strucured lipids allow fat, INFORM, vol. 8, No. 10, Oct. 1997.
http://www.umm.edu/home>medical reference>alternative/ complimentarymedicine>tableofcontents>depletions> antacidsaluminumcalciummagnediumcontainingpreparationscl. htm, Univ. of Maryland Medical Center Website.
Nutraingredients-usa.com article, published Jul. 2, 2003. (no author).
Enzymoted information from enyzmotec.com, pp. 5-7, retrieved Jun. 9, 2009.
International Preliminary Report on Patentability PCT/IL04/00960 dated Dec. 21, 2005.
Written Opinion for PCT/IL2004/000960 received Feb. 22, 2005.
A. Lucas et al., Randomized controlled trial of a synthetic triglyceride milk formula for preterm infants, Archives of Disease in Childhood, 1997, pp. F178-F184, vol. 77.
www.PreparedFoods.com, Nov. 1999.
XP-002315599, Jul. 4, 2003, Food Ingredients First.com.
Kennedy, Kathy et al, Double-blind, randomized trial of a synthetic triacylglycerol in formula-fed term infants: effects on stool biochemistry, stool characteristics, and bone mineralization 1-3, pp. 920, 1999, The American Journal of Clinical Nutrition.
Carnielli, Virgilio P et al, Feeding premature newborn infants palmitic acid in amounts and stereoisomeric position similar to that of human milk: effects on fat and mineral balance 1-3, Jul. 21, 2010, pp. 1037, The American Journal of Clinical Nutricial.
Carnielli, Virgilio P et al, Structural Position and Amount of Palmitric Acid in Infant Formulas: Effects on Fat, Fatty Acid, and Mineral Balance, Journal of Pediatric Gastroenterology & Nutrition: Dec. 1996—vol. 23—Issue 5—pp. 553-560.
Wells, John, Infant and follow-on formulas: the next decade, Jul. 21, 2010, BNF Nutrition Bulletin, vol. 23.
Quinlan P., Structuring Fats for Incorporation into Infant Formulas, Jul. 21, 2010, Fats in Infant Formulas.
Zampelas A. et al, The effect of triacylglycerol fatty acid positional distribution on postprandial plasma metabolite and hormone responses in normal adult men, British Journal of Nutrition (1994) 71, 401-410.
Martin, JC et al, Triacylglycerol structure of human colostrum and mature milk, Lipids, Jul. 1993, 28(7): 637-43.
Kavanagh, A.R. A breakthrough in infant formula fats, 1997, vol. 4, No. 3.
Innis, Sheila M. et al, Structured Triacylglycerols in Infant Nutrition and Metabolism, 1998 by AOCS Press, Department of Paediatrics.
Denke, Margo A. et al, Short-Term Dietary Calcium Fortification Increases Fecal Saturated Fat Content and Reduces Serum Lipids in Men, 1993, American Journal of Nutrition 123:1047-1053.
Chappell, J.E., Fatty acid balance studies in premature infants fed human milk or formula: Effect of calcium supplementation, 1986; 108:439-447, Fetal and Neonatal Medicine.
Kurvinen et al, "Molecular Weight Distribution and Regioisomeric Structure of Triacylglycerols in Some Common Human Milk Substitutes", JAOCS, vol. 79, No. 1, 2002, pp. 13 to 22.
Innis et al, "Saturated fatty acid chain length and positional distribution in infants formuls: effects on grown and plasma lipids and ketones in piglets1-3", Am J. Clin Nutr. 1993, vol. 57, pp. 382-390.
Carnielli et al, "Effect of dietary triacylglycrol fatty acid positional distribution on plasma lipid classes and their fatty acid composition in preterm infants1-3", J. Clin Nutr. 1995, vol. 62, pp. 776-781.
Submission to US FDA for GRAS Exemption Claim for Betapol dated May 28, 2003, GRN No. 131, available at http://www.accessdata.fda.gov/scripts/fcn/gras_notices/309841A.PDF.
Croklaan, Notice of opposition to a European patent No. 1,681,945. Dec. 2011.

* cited by examiner

LIPID PREPARATION FOR ENHANCING MINERAL ABSORPTION

FIELD OF THE INVENTION

The present invention relates to the field of nutritional foods, or food supplements, aiming to provide the population with dietary ingredients that facilitate and assist the intake and absorption of minerals, in order to maintain a well balanced diet and prevent and/or treat health disorders related to the lack thereof.

BACKGROUND OF THE INVENTION

All publications mentioned throughout this application are fully incorporated herein by reference, including all references cited therein.

Lipids in general are the building blocks of life. They are used as building blocks of membranes, cells and tissues, as energy sources, either immediate or stored, as precursors to a variety of other bio-molecules, as well as biochemical signals. In all biochemical processes lipids have an important role.

Many lipids, and especially triglycerides, are consumed in the human nutrition on a daily basis. In most cases, these lipids are metabolized and used for energy storage, as precursors for the biosynthesis of other lipids or bio-molecules. Whatever the fate of the lipids in the metabolic pathways, during and after their consumption, they interact with other nutrients or their metabolic products.

Fatty acids in human milk fat have a highly specific positional distribution on the glycerol backbone. This specific configuration is known to have a major contribution to the efficiency of nutrient absorption.

Palmitic acid (C16:0) is the predominant saturated fatty acid in mature human milk, constituting 20-25% of the fatty acids. 70-75% of this fatty acid is esterified at the sn-2 position of the triglycerides. In contrast, palmitic acid present in vegetable oils, which are most commonly used in the manufacture of infant formulas, is esterified at the sn-1 and sn-3 positions, while the sn-2 position is predominantly occupied by unsaturated fatty acids. The reason for the preferential esterification of palmitic acid to the sn-2 position of glycerol during the synthesis of triglycerides in the mammary gland in uncertain.

Several studies have demonstrated the preferential absorption of palmitic acid when present at the triglyceride sn-2 position [Lien E L. et al. (1997) *J. Ped. Gastr. Nutr.;* 52(2): 167-174; Carnielli V P. et al. (1995) *Am. J. Clin. Nutr.;* 61:1037-1042; Innis S M. et al. (1993) *Am. J. Clin. Nutr.;* 57:382-390; Filer L. J. et al. (1969) *J. Nutr.;* 99:293-8]. The greater absorption of fat and calcium in breast-fed infants compared with those fed formula has been ascribed to two factors: the presence in breast milk of a lipolytic enzyme (the bile salt-stimulated lipase) and the relatively high proportion of palmitic acid at the sn-2 position of the triglyceride [Hernell O. et al. (1988) *Perinatal Nutrition.* New York: Academic Press.; 259-272; Wang C S. et al. (1983) *J. Biol. Chem.;* 258:9197-9202]. Higher palmitic acid absorption was obtained with formulas rich in palmitic acid esterified in the sn-2 position of the triglycerides, than with those containing palmitic acid predominantly esterified in the sn-1,3 position [López-López A. et al. (2001) *Early Hum. Dev.;* 65:S83-S94].

Calcium Absorption

During the first year of life, an infant's birth weight triples and the length is increased by 50%. To meet the requirements of their rapidly expanding skeletal mass, growing infants require a bioavailable source of calcium. For formula-fed infants, availability of calcium depends on the composition of the formula [Ostrom K M. et al. (2002) *J. Am. Coll. Nutr.;* 21(6):564-569].

The digestion of triglycerides involves lipolysis at the sn-1 and 3 positions and formation of free fatty acids and 2-monoglycerides. When palmitic acid is located at the sn-1,3 positions, as is the case in most infant formulas, it is released as free fatty acid which tends to form insoluble calcium soaps. In contrast, palmitic acid as 2-monoglyceride, as in human milk, is unavailable to form calcium soaps [Small D M. (1991) *Annu. Rev. Nutr.;* 11:413-434].

Several studies have shown a correlation between formulas containing high levels of palmitic acid situated at the sn-1,3 positions of the triglyceride and reduction in calcium absorption [Nelson S E. et al. (1998) *J. Amer. Coll. Nutr.;* 17:327-332; Lucas A. et al. (1997) *Arch. Dis. Child.;* 77:F178-F187; Carnielli V P. et al. (1996) *J. Pediatr. Gastroenterol. Nutr.* 23:553-560; Ostrom (2002) id ibid.; Hanna (1970) id ibid.]. In addition, it was shown that dietary triglycerides containing palmitic acid predominantly at the sn-2 position, as in human milk, have significant beneficial effects on the intestinal absorption of fat and calcium in healthy term infants as well as in preterm infants [Carnielli (1996) id ibid.; Carnielli (1995) id ibid.; Lucas (1997) id ibid.]. Infants fed a formula containing high levels of palmitic acid at the sn-1,3 positions showed greater fecal excursion of calcium and, hence, lower percentage absorption of calcium compared to infants fed a formula containing low levels of palmitic acid [Nelson S E. et al. (1996) *Am. J. Clin. Nutr.;* 64:291-296.]. Fecal excretion of calcium was closely related to the fecal excretion of fat. This study also showed that urinary phosphorus excretion increased and phosphorus retention decreased when infants were fed the formula containing high levels of palmitic acid at the sn-1,3 positions. These findings presumably reflect lower availability of calcium for deposition in bones.

Another important issue which is associated with formula feeding is constipation in both term and preterm infants which, in the latter, can lead to life threatening complications. By contrast, constipation is rare in breast fed term infants. A study comparing breast fed and formula fed infant stool hardness and composition showed that calcium fatty acid soaps are positively correlated to stool hardness. Stools from formula-fed infants were significantly harder than those of the breast-fed infants suggesting different handling of saturated fatty acids [Quinlan P T. et al. (1995) *J. Pediatr. Gastr. and Nutr.;* 20:81-90].

In an attempt to overcome the decreased calcium absorption and hard stool phenomena, infant formula manufacturers tend to deviate from the fatty acid profile by replacing palmitic acid with lauric acid and, in some cases, by increasing the polyunsaturated fatty acid content. Studies have shown that fatty acid composition of the diet influences the fatty acid composition of developing infant tissue [Widdowson E. M. (1975) *Br. Med. J.;* 1:633-5; Carlson S E. et al. (1986) *Am. J. Clin. Nutr.;* 44:798-804; Innis S M. et al. (1990) Am. J. Clin. Nutr.; 5:994-1000; Koletzko B. et al. (1989) *Eur. J. Pediatr.;* 148:669-75] and thus the lipoprotein and lipid metabolism differ between breast-fed and formula-fed infants [Putnam J. C. et al. (1982) *Am. J. Clin. Nutr.;* 36:106-114; Innis S M. et al. (1992) *Am. Coll. Nutr.;* 11:63S-8S; Van Biervliet J P. et al. (1981) *Acta. Paediatr. Scand.;* 70:851-6].

Innis and colleagues [Innis (1993) id ibid.], when comparing three formulas containing similar amounts of saturated fatty acids—C8-C14, C16 from palm oil (predominantly in the sn-1,3 positions), or C16 from synthesized triglyceride (predominantly in the sn-2 position)—showed that the chain length of saturated fatty acids in infant formula influences the metabolism of the dietary oleic, linoleic and alpha-linolenic acids. This study also showed that the sn-2 configuration of C16 in human milk triglycerides seems to have unique properties that extend beyond absorption. These include effects on HDL and cholesterol concentrations, and the cholesterol ester fatty acid composition.

The impact of soap formation on calcium absorption can be significant. Many infant formulas contain sufficient saturated fatty acids to form soaps with virtually all the calcium available.

U.S. Pat. No. 4,876,107 (corresponding to EP 0 209 327) describes a substitute milk fat composition which is suitable as replacement fat in infant formulations. In this fat composition the total palmitic acid residues present is as high as 45%, with at least half of the fatty acid residues at the 2-position of the glycerol backbone being palmitic. The product has about 27% palmitic acid residues at the 1- and 3-positions, and the other substituents at the 1- and 3-positions are mainly unsaturated $C_{16}$ and $C_{18}$ fatty acid moieties. The fat composition is prepared by a specific process, in the presence of hexane. Rather high levels of the fat compositions are required for the preparation of infant formulations.

EP 0 495 456 also discloses substitute milk fat compositions. These compositions have a saturated fatty acid content at the sn-2 position of at least 40%, most of which palmitic acid residues, and contain 0.2-7% linolenic acid moieties, 70% of which are bonded at the 1- and 3-positions of the glycerol moieties, the remaining acid moieties at the 1- and 3-positions, other than unsaturated fatty acids, are saturated $C_4$-$C_{12}$ fatty acids.

U.S. Pat. No. 5,658,768 discloses a multiple-step process for preparing triglyceride compositions in which more than 40% of the saturated fatty acid moieties are at the 2-position. Many of the steps involve enzymatic modifications.

Furthermore, lipids in the form of fatty acids hydrolyzed from triglycerides interact with minerals, either obtained from the diet or present in the body, especially calcium ions. This interaction can lead, in some cases, to the complexation for example of fatty acids and calcium ions to form insoluble complexes, which cannot be utilized by the human body and are secreted, resulting in their loss. This is actually a loss of important nutrients, since calcium is essential for skeleton building and other bodily functions, while fatty acids are an important source of energy and precursors of other lipids and nutrients.

Thus, infants and young children until the age of 3 are advised to base their nutrition on human breast milk or its replacements in the form of infant formulas, since these include in their ingredients a fat portion which mimics to some extent the fat composition of human breast milk. However, many infants and young children do not have access to such fat, either because they do not breast feed or consume infant formulas, or they consume infant formulas without human milk fat replacements, or even, above a certain age, because they supplement their nutrition with other foods, besides breast milk or infant formula. Moreover, many food products allegedly designed for the consumption of infants and young children, such as cereals, dairy products, and biscuits, are based on vegetable oils which have nothing in common with breast milk fat.

In all these scenarios, infants and young children consume fats and oils which upon their digestion create insoluble complexes with essential calcium which in turn are secreted, leading to the loss of both calcium and energy supplying lipids. This is very detrimental, since calcium is an essential nutrient during child development, in particular for skeletogenesis, i.e., bone formation.

For adults, dietary supplementation of all minerals and particularly calcium is carried out using commercial products in which the mineral can appear in different salt forms, for example calcium is in the form of calcium carbonate, calcium alginate, calcium picolinate, calcium from corals, and many other forms. In many cases, this supplemented calcium is not absorbed by the body and is secreted, or it causes digestive problems, such as constipation.

Therefore, although the dietary supplementation of minerals is needed for infants and young children, as well as adults, especially women over the age of 45, in order to treat or prevent disorders or conditions caused by mineral depletion, it is not fulfilled in a satisfactory manner.

Thus, it is an object of the present invention to provide a dietary ingredient comprising edible lipid(s), wherein said lipid has the property of enhancing the absorption and intake of minerals. Other uses and objects of the invention will become clear as the description proceeds.

SUMMARY OF THE INVENTION

The present invention relates to a dietary ingredient comprising at least one edible lipid, wherein said lipid does not inhibit mineral absorption, enhances mineral absorption and intake.

In particular, the lipid comprised in the dietary ingredient of the invention is selected from the group consisting of chemically or enzymatically synthesized synthetic oils, particularly glyceride-based lipids with high levels of mono- or polyunsaturated fatty acids at positions sn-1 and sn-3 of the glycerol backbone, vegetable- and plant-derived, preferably flax and canola oils, short and medium chains lipids, preferably MCT and oils mimicking the triglyceride composition of human mother's milk fat.

The dietary ingredient of the invention is preferably a mimetic of human mother's milk fat.

The said minerals are preferably selected from the group consisting of calcium, magnesium, iron and other divalent minerals.

The dietary ingredient of the invention may further comprise at least one of edible additives, emulsifiers or carriers.

The dietary ingredient of the invention is particularly intended for use in enhancing calcium absorption.

In another embodiment, the dietary ingredient of the invention may be used for the prevention and/or treatment of disorders associated with any one of depletion of bone calcium and bone density, particularly for the prevention and/or treatment of osteoporosis, for the enhancement of bone formation and bone mass maximization and for the enhancement of bone formation in infants and young children.

The dietary ingredient of the invention may also be used for enhancement of energy intake by infants and children.

In a further embodiment, the invention relates to a food article comprising the dietary ingredient of the invention.

The food article of the invention may be selected from infant formulas and food, bakery products, including bread, particularly biscuits and pastries, dairy products, including milk and dairy drinks, ice cream, cereal products, sauces, spreads, including margarine, oils and fats, soy products, meat products, fried food products, confectionery products, candy bars, candies and chocolates, snacks, drinks and shakes, instant drink products, prepared foods for infants and young children and for adults, including prepared cooked mashed vegetables and/or fruits, condiment products, cooking oils and fats and meat products.

In yet a further embodiment, the invention relates to a dietary supplement comprising the lipid ingredient of the invention, and to use of the lipid ingredient of the invention as a carrier for dietary supplements.

DETAILED DESCRIPTION OF THE INVENTION

The present invention describes food products based on lipids mimic that replaces most or all of the fats and oils used in the preparation and formulation of these food products.

In a first aspect, the present invention provides a dietary ingredient comprising at least one edible lipid, wherein said lipid has the property of enhancing the absorption and intake of minerals.

Lipids, under the scope of this invention, include mainly, but are not limited to triglycerides and derivatives. Essentially, the invention is mainly concerned with dietary ingredient containing lipids which do not inhibit calcium absorption and promote calcium and energy intake, calcium absorption and mass bone peak maximization.

Such lipids may be based on synthetic oils (which can be produced both chemically and, preferably, enzymatically), particularly glyceride-based lipids with high levels of mono- or polyunsaturated fatty acids at positions sn-1 and sn-3 of the glycerol backbone. Lipids of interest also include certain vegetable-derived or other oils (flax oil, canola, etc.). Short and medium chains lipids, such as MCT oil can also be used, as such lipids, although saturated, do not cause the formation of insoluble calcium salts.

Also of particular interest are lipids which are oils mimicking the triglyceride composition of human breast milk fat. An example for such lipids is applicant's InFat™ [co-owned, co-pending PCT Application claiming priority from IL158555], which has a high level of palmitic acid at the sn-2 position of the triglycerides, and a high level of unsaturated fatty acids at sn positions 1 and 3, preferably over 50%. Another example for such human milk fat mimetic lipid is the commercially available Betapol™ (Loders Croklaan).

The unique structure of InFat™ and other human milk fat mimetics results in the release of unsaturated fatty acids from the sn-1 and 3 positions of the fat's triglycerides during their enzymatic digestion. These fatty acids either do not generate, or generate in very small amounts, indigestible calcium complexes, hence not causing the loss of both calcium and energy. The glycerides with the palmitic acid moieties play other important roles in the nutrition of infants. Therefore, the absorption of calcium is not adversely affected, as may be with other types of fats and oils, as mentioned above.

The main property of the dietary ingredient of the invention is its ability to not inhibit and even enhance the absorption of minerals, such as calcium, magnesium, iron, and other divalent nutritional minerals. Said minerals may be provided by other foods, or it may be obtained in admixture with the dietary ingredient of the invention.

Thus, in one embodiment, the dietary ingredient of the invention may optionally further comprise divalent nutritional minerals, preferably] calcium and iron.

In another embodiment, the dietary ingredient of the invention can optionally include other nutrients, such as other minerals or vitamins, or a combination of both.

The present invention also teaches a method of preparation of the dietary ingredient of the invention, comprising admixing an edible lipid, and optionally calcium, and at least one of additives, emulsifiers or carriers, wherein said edible lipid is a mimetic substitute of human breast milk.

The dietary ingredient of the invention shall be used in the preparation of any food product which contains fat as one of its ingredients or components. Thus, the dietary ingredient of the invention may replace some, most or all fat content of the food product.

This food product may be aimed and consumed by infants and young children, such as formulas, bakery products, dairy products, sauces, spreads, oils and fats, soy products, meat products, fried food products, milk and dairy drinks, biscuits, candy, bars, cereals, instant drink products, prepared cooked mashed vegetables and/or fruits, etc.

Alternatively, this food product is any food product, such as bakery products, confectionary products, condiments, sauces, dairy products, ice cream, biscuits, soy products, fried food products, pastry and bread, sauces, condiments, oils and fats products, spreads, soy products, meat products, margarines, cereals, drinks and shakes, infant formulas and foods, bars, snacks, candies or chocolate products. Thus, the dietary ingredient provided by the invention is to be included in food products for adult consumption.

In another aspect, the dietary ingredient of the invention is intended for use in the prevention and/or treatment of disorders associated with depletion of bone calcium or conditions related to decrease in bone density. In particular, the dietary ingredient of the invention is for use in the prevention and/or treatment of osteoporosis.

A significant percentage of the adult population, in particular pre- and post-menopause women, suffers from osteoporosis, a common disorder caused by hormonal-related depletion of calcium in the bones. Consequently, calcium supplements are the biggest selling supplement in the world. However, as described above, in many cases these calcium supplements do not supply this essential nutrient effectively, due to poor absorption and, in some cases, they may even cause digestive disorders.

Hence, the dietary ingredient of the invention aims to solve this problem, by providing the means, i.e., the lipids that allow and facilitate calcium absorption, as described above. Consequently, the consumption of food products based on human milk fat mimetics, such as Applicant's InFat, or the other lipids of interest described above, as the major, if not only, fat source will facilitate improved absorption of calcium either from food sources, or from calcium supplements.

Additionally, the production of food products containing fats and/or oils based on the lipid comprised in the dietary ingredient of the invention shall motivate the general population to incorporate such products in their nutrition, in order to assist in the absorption and bio-availability of a variety of supplemented nutrients, particularly minerals and especially calcium. This shall enhance the absorption and bio-availability of both supplemented and naturally occurring nutrients in the normal human nutrition.

In a further aspect, the dietary ingredient of the invention is also intended for use in the enhancement of bone formation.

As mentioned before, calcium is an important nutrient during child development, especially for proper skeletogenesis. Therefore, dietary supplements containing calcium should be an integral part of children's nutrition, preferably infants and children until the age of 3. Lately, clinical data suggest that calcium supplementation is recommended also for adolescents who are at a crucial age, since at this age window, and until the age of about 25, adolescents reach the peak of their bone mass. After this stage, the bones will start a slow and continuous biochemical process in which they start to deplete and deteriorate. It is known that the higher the bone mass built early in life, the less prone would the individual become to health disorders related to bone depletion, such as osteoporosis. Hence, it is of great health value and importance to maximize the bone mass peak. This can be achieved by balanced nutrition, and/or calcium supplementation, together with specific vitamins and other nutrients. It is a purpose of this invention to provide a dietary lipid ingredient that would ensure maximal calcium absorption and/or lack of inhibition of calcium absorption through the replacement of unhealthy oils and fats which promote the secretion of calcium, as well as other important minerals. Such oils and fats, characterized by relatively high degree of fatty acid saturation at the sn-1 and 3 positions are becoming more and more abundant in the diets of young children, adolescents and young people. The lipids of the invention, when consumed routinely in different food products or as dietary supplements together with mineral supplementation may increase the calcium intake and hence bone mass peak, resulting in a preventive condition to bone depletion disorders in later years of life.

The use of such lipids by the young population may also improve intake of other divalent minerals, such as iron and magnesium, the earlier important for cognitive development and function.

The enhanced absorption and bio-availability of nutrients will optimize their preservation and maximize the energy provided by the same. This enhanced absorption and bio-availability will also reduce disorders, such as digestive disorders, related to the loss of valuable nutrients.

The importance of calcium for the human body goes beyond skeletal development and the treatment or prevention of osteoporosis. Calcium is one of the most important minerals used by the organism to perform numerous biochemical processes. It is important in ion pump functions, as a co-factor for enzymes, as a cross-membrane potential mediator, etc. Thus, calcium depletion has an adverse effect on all these processes and functions of the body. Therefore, the dietary ingredient of the invention is highly recommended as a dietary supplement in the adult diet.

When used as a dietary supplement, the lipid ingredient of the invention may be particularly suitable for supplements dispensed in an oil-based matrix. In such supplements, the lipid ingredient of the invention can assume a dual function, serving as also the oily carrier, avoiding the need for the oily matrix. Such embodiments may be suitable for many known and used dietary supplements, which are usually dispersed or carried in an oily matrix. In such cases, the oil may diminish or inhibit absorption of calcium from the normal diet.

Thus, lastly, the present invention provides a dietary ingredient for use in the enhancement of energy intake by infants and children.

The present invention is defined by the claims, the contents of which are to be read as included within the disclosure of the specification.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

In the following Examples, InFat can be replaced by any other human milk fat mimetic (e.g. Betapol$^R$), or any of the lipids of interest mentioned above.

Example 1

Infant Formula Based on InFat

An infant formula comprising InFat and additional oils and fats that mimic the human breast milk fat composition that facilitates enhanced calcium intake as well as improved energy preservation (in the form of free fatty acids). The InFat may be used as is or as a blend that would constitute about 10-40% of the formula and would replace most or all other fats and oils from the formula.

As mentioned, InFat is an oil containing over 90% triglycerides. InFat also contains diglycerides. In some formulations, InFat can include up to 3% free fatty acids. The triglycerides of this product are characterized by a high percentage of palmitic acid at the sn-2 position, over 60%, from the total palmitic acid in this oil. The sn-1 and 3 positions are characterized by a high percent of oleic acid and other unsaturated fatty acids.

Example 2

Biscuits and Pastry for Infants and Young Children

A biscuit or pastry product designed nutritionally for infants and young children. The biscuit has several percents of oils and fats, all or most are InFat, thus ensuring that while eating such biscuits or pastries the infant will not lose valuable calcium and energy. Such product may include 1 to 15% fat or oil, preferably 3 to 9%.

In a specific recipe, biscuits were produced from dough comprising the following ingredients: Wheat flour (41%), Cane sugar (20.5%), Water (25.8%), InFat (8.2%), Corn starch (2.9%), and Leavening agent (1.6%). Another recipe includes Wheat flour (42.2%), Cane sugar (21.1%), Water (16.8%), InFat (8.4%), Corn starch (11.0%), Leavening agent (0.3%), and Salt (0.2%).

Such biscuits would suit infants and young children in their ability to crumble when in contact with saliva in the infant's mouth and are easy for chewing and nibbling. The biscuits were produced and were tested by a tasting panel to give satisfactory results in both taste and texture.

Example 3

Dairy Products for Infants and Children for Enhanced Calcium Intake

A dairy product, such as yoghurt, designed nutritionally for infants and young children. The dairy product, such as yoghurt, has several percents of oils or fats, all or most are InFat, thus ensuring that while eating such dairy product the infant will not lose valuable calcium and energy. Such product may include 0.5 to 15% fat or oil, preferably 1.5 to 10%. The dairy product may also be enriched with calcium and iron supplements.

Example 4

Cereal Products for Infants and Children for Enhanced Calcium Intake

A cereal product, such as oatmeal or rice cereal, designed nutritionally for infants and young children. The cereal product has several percents of oils or fats, all or most are InFat, thus ensuring that while eating such cereal product the infant will not lose valuable calcium and energy. Such product may include 0.5 to 15% fat or oil, preferably 2 to 7%.

Example 5

Mashed Fruits and/or Vegetables Products for Infants and Children for Enhanced Calcium Intake A mashed fruit or vegetable prepared food product designed nutritionally for infants and young children. The mashed fruit or vegetable prepared product has several percents of oils or fats, all or most are InFat, thus ensuring that while eating such mashed food product the infant will not lose valuable calcium and energy. Such product may include 0.5 to 15% fat or oil, preferably 1 to 7%.

Example 6

Meat Products for Infants and Children for Enhanced Calcium Intake

A mashed meat or soup prepared food product designed nutritionally for infants and young children. The mashed meat or soup prepared product has several percents of oils or fats, all or most are InFat, thus ensuring that while eating such meat product the infant will not lose valuable calcium and energy. Such product may include 0.5 to 15% fat or oil, preferably 3 to 10%.

Example 7

Condiment Products for Infants and Children for Enhanced Calcium Intake

A condiment food product, such as ketchup or mayonnaise for example, designed nutritionally for infants and young children. The condiment product, such as ketchup, has several percents of oils or fats, all or most are InFat, thus ensuring that while eating such condiment product the infant will not lose valuable calcium and energy. Such product may include 0.5 to 15% fat or oil, preferably 1 to 7%.

Example 8

Sweet Spreads Products for Infants and Children for Enhanced Calcium Intake A sweet spread food product, such as chocolate spread, jam or peanut butter flavored spread, designed nutritionally for infants and young children. The sweet spread product has several percents of oils or fats, all or most are InFat, thus ensuring that while eating such sweet spread product the infant will not lose valuable calcium and energy. Such product may include 0.5 to 30% fat or oil, preferably 5 to 15%.

Example 9

Cooking Oils/Fats for Infants and Children for Enhanced Calcium Intake

A cooking oil or fat spread product designed nutritionally for infants and young children. The cooking oil or fat spread product has several percents of oils or fats, all or most are InFat, thus ensuring that while eating such oil or spread product the infant will not lose valuable calcium and energy. Such product may include 15 to 99% fat or oil, preferably 45 to 95%.

Example 10

Biscuits and Pastry for Adult Nutrition for Enhanced Calcium Intake

A biscuit or pastry product designed nutritionally for adults. The biscuit has several percents of oils and fats, all or most are InFat, thus ensuring that while eating such biscuits or pastries the adult will not lose valuable calcium. Such product may include 1 to 15% fat or oil, preferably 3 to 7%.

Example 11

Dairy Products for Adult Nutrition for Enhanced Calcium Intake

A dairy product, such as yoghurt, designed nutritionally for adults. The dairy product, such as yoghurt, has several percents of oils or fats, all or most are InFat, thus ensuring that while eating such dairy product the adults will not lose valuable calcium. Such product may include 0.5 to 15% fat or oil, preferably 1 to 10%.

Example 12

Cereals Products for Adults for Enhanced Calcium Intake

A cereal product, such as corn flakes and granola, designed nutritionally for adults. The cereal product has several percents of oils or fats, all or most are InFat, thus ensuring that while eating such cereal product the adults will not lose valuable calcium. Such product may include 0.5 to 15% fat or oil, preferably 2 to 7%.

Example 13

Meat Products for Adults for Enhanced Calcium Intake

A meat food product, such as sausage or hamburgers, designed nutritionally for adults. The meat product has several percents of oils or fats, all or most are InFat, thus ensuring that while eating such meat product the adults will not lose valuable calcium. Such product may include 0.5 to 25% fat or oil, preferably 3 to 10%.

Example 14

Prepared Food Products for Adults for Enhanced Calcium Intake

A prepared food product, such as hamburgers, vegetable dishes, french fries, pizza, and alike, designed nutritionally for adults. The prepared food product has several percents of oils or fats, all or most are InFat, thus ensuring that while eating such prepared food product the adults will not lose valuable calcium. Such product may include 0.5 to 25% fat or oil, preferably 2 to 7%.

Example 15

Condiment Products for Adults for Enhanced Calcium Intake

A condiment food product, such as ketchup, mayonnaise, salad dressing, or mustard, designed nutritionally for adults. The condiment product, such as ketchup, has several percents of oils or fats, all or most are InFat, thus ensuring that while eating such condiment product the adult will not lose valuable calcium. Such product may include 0.5 to 15% fat or oil, preferably 2 to 7%.

Example 16

Cooking Oils/Fats for Adults for Enhanced Calcium Intake

A cooking oil or fat spread product designed nutritionally for adults. The cooking oil or fat spread product has several percents of oils or fats, all or most are InFat, thus ensuring that while eating such oil or spread product the adult will not lose valuable calcium. Such product may include 15 to 100% fat or oil, preferably 25 to 95%.

Example 17

Condiment Products for Adults for Enhanced Calcium Intake

A condiment food product, such as ketchup, mayonnaise, salad dressing, or mustard, designed nutritionally for adults. The condiment product, such as ketchup, has several percents of oils or fats, all or most are InFat, thus ensuring that while eating such condiment product the adult will not lose valuable calcium. Such product may include 0.5 to 15% fat or oil, preferably 2 to 7%. The condiment product is also enriched with calcium, such as calcium phosphate or calcium picolinate, at levels of 0.1% to 5%, preferably 0.5% to 1.5%. The calcium supplement may provide about 500-1500 mg/serving.

The invention claimed is:

1. A method of enhancing dietary calcium absorption, bone formation, and bone mass maximization, in a non-infant child or adult subject, said method comprising administering (1) a food article, excluding infant formula, to said subject, or (2) a lipid-based dietary supplement to said subject, wherein said food ankle or said lipid-based dietary supplement comprises at least one edible lipid that enhances calcium absorption and intake, and wherein said edible lipid is selected from the group consisting of chemically and enzymatically synthesized vegetable- and plant-derived synthetic oils, said edible lipid being a glyceride-based lipid having over 50% of mono- or polyunsaturated fatty acids at positions sn-1 and sn-3 and a high level of palmitic acid at position sn-2 of a glycerol backbone, wherein said edible lipid is free of all or most of unhealthy oils and fats, which unhealthy oils and fats have high degree of fatty acid saturation at the sn-1 and sn-3 positions, the edible lipid constituting at least part of a fat content of the food article or of the dietary supplement; wherein the food article or the lipid-based dietary supplement further comprises calcium and wherein the food article or the dietary supplement is administered routinely to the non-infant child or adult subject, thereby enhancing dietary calcium absorption, bone formation, and bone mass maximization in the non-infant child or adult subject.

2. The method of claim 1, wherein said food article is selected from the group consisting of bakery products, dairy products, ice cream, cereal products, sauces, spreads, oils and fats, soy products, meat products, fried food products, confectionery products, candy bars, candies and chocolates, snacks, drinks and shakes, instant drink, products, prepared foods for young children and for adults, and condiment products, wherein the food article is not an infant formula.

3. The method of claim 2, wherein said food article is a calcium supplement, said administering thereby supplementing said non-infant child or adult subject with calcium.

4. The method of claim 2, wherein said edible lipid replaces unhealthy oils and fats, having a relatively high degree of fatty acid saturation at the sn-1 and sn-3 positions, present in diets of non-infant young children, adolescents, and young people.

5. The method of claim 2, wherein said bakery products are selected from the group consisting of bread, biscuits, and pasteries.

6. The method of claim 2, wherein said dairy products are selected from the group consisting of milk and dairy drinks.

7. The method of claim 3, wherein said edible lipid of said food article serves as a carrier for calcium.

8. The method of claim 1, wherein said edible lipid administered is a glyceride-based lipid having over 50% of mono- or polyunsaturated fatty acids at positions sn-1 and sn-3 of the glycerol backbone and a high level of palmitic acid at position sn-2 of the glycerol backbone which, during digestion, does not generate or generates in very small amounts indigestible calcium complexes.

9. The method of claim 1, wherein said plant-derived synthetic oil is flax oil or canola oil.

* * * * *

UNITED STATES PATENT AND TRADEMARK OFFICE
CERTIFICATE OF CORRECTION

| | | |
|---|---|---|
| PATENT NO. | : 8,618,050 B2 | Page 1 of 1 |
| APPLICATION NO. | : 10/576239 | |
| DATED | : December 31, 2013 | |
| INVENTOR(S) | : Avidor Shulman et al. | |

It is certified that error appears in the above-identified patent and that said Letters Patent is hereby corrected as shown below:

In the Claims:

Column 12, Claim 1, line 7, change "ankle" to --article--.

Signed and Sealed this
Twenty-fifth Day of November, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,618,050 B2                                         Page 1 of 1
APPLICATION NO.  : 10/576239
DATED            : December 31, 2013
INVENTOR(S)      : Shulman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1053 days.

Signed and Sealed this
Twenty-second Day of September, 2015

Michelle K. Lee
*Director of the United States Patent and Trademark Office*